(12) United States Patent  
Pillari

(10) Patent No.: US 7,682,324 B2  
(45) Date of Patent: Mar. 23, 2010

(54) BREAST AND BOTTLE FEEDING INFANT HEAD SUPPORT

(76) Inventor: Elizabeth M. Pillari, 7 Bermet Ct., Tinton Falls, NJ (US) 07724

( * ) Notice: Subject to any disclaimer, the term of this patent is extended or adjusted under 35 U.S.C. 154(b) by 0 days.

(21) Appl. No.: 12/213,262

(22) Filed: Jun. 17, 2008

(65) Prior Publication Data  
US 2008/0250567 A1    Oct. 16, 2008

Related U.S. Application Data

(63) Continuation-in-part of application No. 11/790,930, filed on Apr. 30, 2007, now abandoned, which is a continuation of application No. 10/115,068, filed on Apr. 4, 2002, now abandoned.

(51) Int. Cl.  
*A61F 5/00* (2006.01)

(52) U.S. Cl. .......................................... 602/20; 602/22

(58) Field of Classification Search ................ 602/4–5, 602/20–23, 60–62; 5/630; 128/845, 846, 128/856  
See application file for complete search history.

(56) References Cited

U.S. PATENT DOCUMENTS

| | | | | |
|---|---|---|---|---|
| 3,451,071 A | * | 6/1969 | Whiteley | 5/630 |
| 4,048,818 A | * | 9/1977 | Cueman | 66/172 E |
| 4,424,809 A | * | 1/1984 | Yovankin | 602/62 |
| 4,832,010 A | * | 5/1989 | Lerman | 602/63 |
| 6,224,564 B1 | * | 5/2001 | Korobow | 602/62 |

* cited by examiner

*Primary Examiner*—Michael A. Brown  
(74) *Attorney, Agent, or Firm*—Charles I. Brodsky

(57) ABSTRACT

A breast and bottle feeding infant head support including a slip-on sleeve open at opposite ends and inclusive of inner and outer linings forming first and second outwardly opposing face surfaces of predetermined length and width, and a cushion insert between the inner and outer linings forming at least one of the outwardly opposing face surfaces wherein the sleeve, when worn on the arm, is of a length to extend past the crook of a wearer's elbow and towards the palm of the wearer's hand for the fingers to hold the sleeve in place.

8 Claims, 2 Drawing Sheets

BREAST AND BOTTLE FEEDING INFANT HEAD SUPPORT

CROSS-REFERENCE TO RELATED APPLICATIONS

This application is a continuation in part of application Ser. No. 11/790,930 filed Apr. 30, 2007 now abandoned, which is a continuation of application Ser. No. 10/115,068 filed Apr. 4, 2002 now abandoned.

STATEMENT REGARDING FEDERALLY SPONSORED RESEARCH OR DEVELOPMENT

Research and development of this invention and Application have not been federally sponsored, and no rights are given under any Federal program.

REFERENCE TO A MICROFICHE APPENDIX

NOT APPLICABLE

BACKGROUND OF THE INVENTION

1. Field of the Invention

This invention relates to the breast and bottle feeding of infants, in general, and to a support to make breast and bottle feeding comfortable for both a mother and her baby, in particular.

2. Description of the Related Art

As is well known and understood, in the breast and/or bottle feeding of infants, the baby's head is typically supported against the mother's inside forearm. Experience has shown that with the forearm being firmer than the baby's head, these breast and bottle feedings over time tend to somewhat flatten the head of the infant. Such head, besides being so malleable, also tends to absorb the perspiration built up on the forearm during hot humid weather, especially when the mother wears a short sleeve blouse. These deficiencies and detriments are addressed by the present invention.

SUMMARY OF THE INVENTION

As will become clear from the following description, the present invention comprises a breast and bottle feeding infant head support utilizing a slip-on sleeve open at the opposite ends thereof, and inclusive of inner and outer linings forming first and second opposing face surfaces of predetermined length and width. A cushion insert is added according to the invention, between the inner and outer linings beneath one of the opposing face surfaces. When the sleeve is worn on the arm, and selected of a length to extend past the crook of a wearer's elbow, the cushion support gives to the sleeve a padded feeling providing a comfort both for the mother and for her baby. In a preferred embodiment to be described, the slip-on sleeve is of a durable fabric material, softly absorbent, and washable—as of a cotton fabric, for example. At the same time, the cushion insert preferably resilient, as a foam, for instance. Selected of a width substantially equal to the predetermined widths of the first and second opposing face surfaces, the cushion insert of the invention could similarly be selected of a length substantially equal to the predetermined lengths of the first and second opposing surfaces, or of a length somewhat less. In such latter instance, the slip-on sleeve may extend from past the crook of the elbow towards the palm of the hand, where the fingers could encircle it to hold it in place, without grasping onto the cushion insert.

In a further embodiment of the invention, a second insert may be added, between the inner and outer linings beneath the other of the two opposing face surfaces, so that the slip-on sleeve could be alternated in wearing with first one, then the other, surface supporting the infant's head during alternative feedings. There, too, the second cushion insert could be of comparable lengths and widths to that of the face surfaces, or of differing length surface if so desired.

As will be appreciated, a cradle essentially is established for supporting the infant's head, in a manner to absorb perspiration, with a soft absorbent fabric, and in a manner to make the breast and bottle feeding a comfort not only for the infant, but for the mother, as well.

BRIEF DESCRIPTION OF THE DRAWINGS

These and other features of the present invention will be more clearly understood from a consideration of the following description, taken in connection with the accompanying drawings, in which.

DETAILED DESCRIPTION OF THE INVENTION

Figure 1:
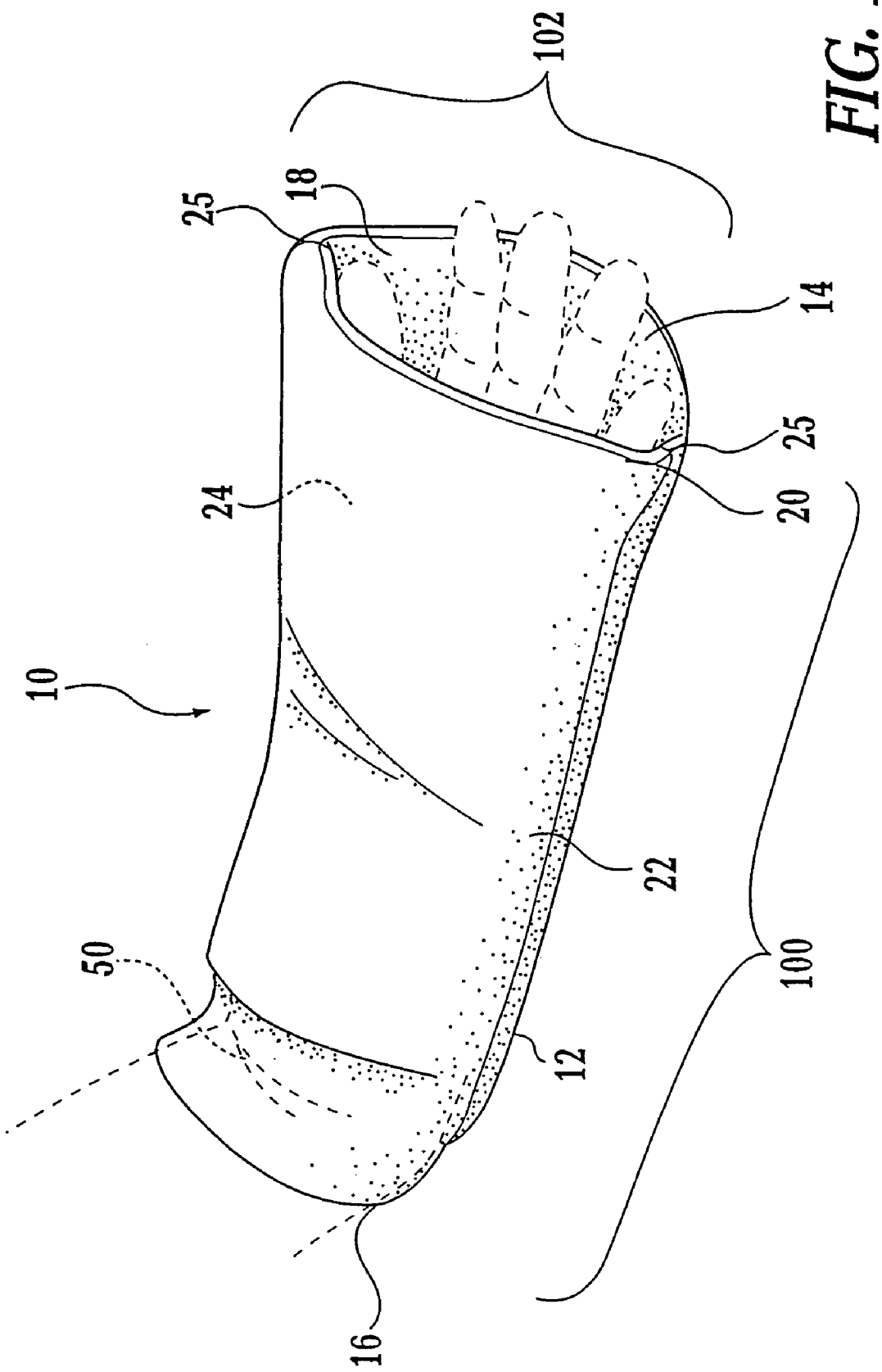
FIG. 1 is a perspective view of a breast and bottle feeding infant head support embodying the invention.
Figure 2:
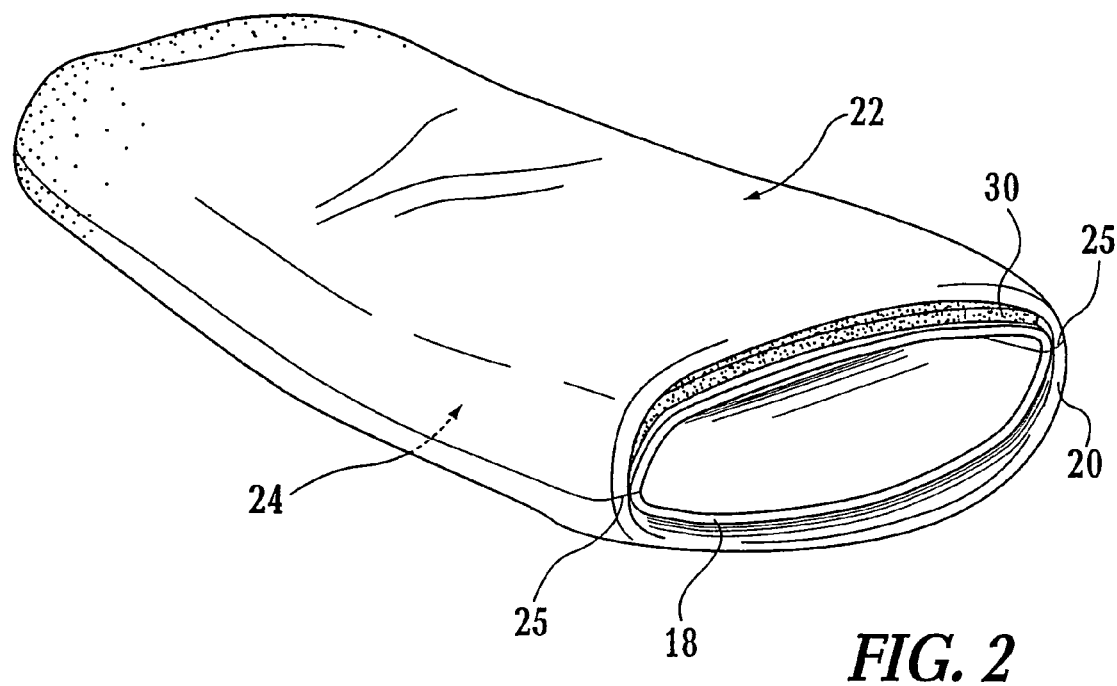
FIGS. 2 and 3 are partial perspective views helpful in an understanding of preferred embodiments of the invention support.

Referring to FIGS. 1 and 2, the breast and bottle feeding infant head support includes a slip-on sleeve 10 of a durable fabric material 12, preferably soft and absorbent, and/or washable, as a cotton fabric. The sleeve 10 is shown open at its opposite ends 14, 16 and includes inner and outer linings 18, 20 which form first and second opposing face surfaces 22, 24 of predetermined length 100 and width 102. The outer lining 20 may be sewn together along its length, and the inner lining 18 sewn to it as by tacking at 25. Between the linings 18, 20, a cushion insert 30 is included, of a resilient material such as a padded foam. As more clearly shown in FIG. 2, such insert is emplaced between the inner and outer linings 18, 20 beneath the face surface 22. Such insert 30 may be of a length substantially equal to the predetermined length 100 of the slip-on sleeve 10, and of a width substantially equal to that of the predetermined width 102. Alternatively, and where desired, the length of the cushion insert 30, on the other hand, may be selected somewhat less than the length 100 of the face surface 22. In either event, the slip-on sleeve 10, when worn on the arm (as shown) is of a length to extend past the crook of a wearer's elbow, shown at 50.

When worn in such manner, the infant's head can be supported along the forearm, or at the crook of the elbow at 50, resting on the surface 22 beneath which the cushion insert 30 sits. In such manner, a comfortable support for the head is provided, and the fabric of which the sleeve 10 is composed absorbs any perspiration that may be present. The resilient nature of the cushion cuddles the newborn and any tendency to flatten the head over time is reduced by virtue of the padded effect.

Figure 3:
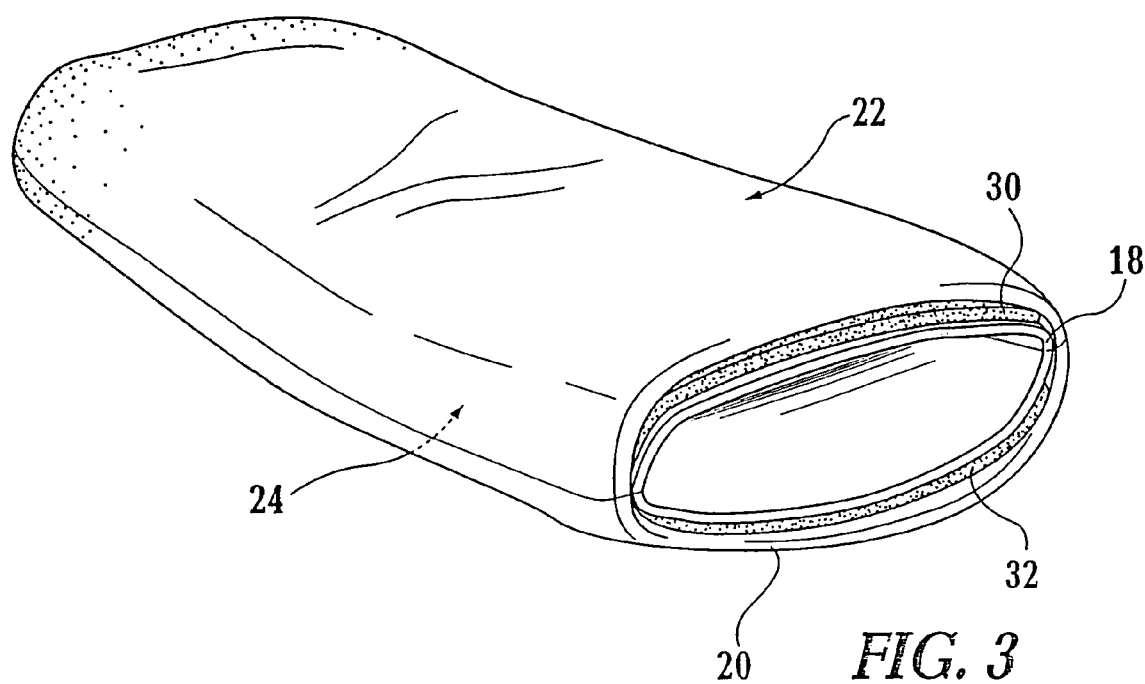

FIG. 3 illustrates the addition of a second cushion insert 32 between the inner and outer linings 18, 20 beneath the opposite face surface 24. Of a comparable length to the cushion insert 30, the second cushion insert 32 could likewise be of a length substantially equal to the length 100 of the face surface 24 in this respect, and of a width 102 substantially equal to the width of the face surface. If of a length somewhat less than the length 100, the second cushion insert 32 will fall short of reaching towards the palm of the wearer's hand, whose fingers could then encircle the fabric end of the sleeve 10. With such a construction, the slip-on sleeve 10 could be worn with the face surface 22 supporting the infant's head on one occasion, and then the face surface 24 provides the support, when the sleeve 10 is rotated in wearing. As with the cushion insert 30, the cushion insert 32 may be of a resilient material such as a padded foam.

In a preferred construction of the invention, the slip-on sleeve 10 is constructed of a polyester MicroVelour fabric while the cushion insert 30 (and the cushion insert 32 where it is employed) is constructed of a hypoallergenic polyurethane. As will be appreciated, the polyester nature of the fabric allows the sleeve to be washable. At the same time, the polyurethane nature of the cushion(s) allows the infant's head to be supported—but because of their resilient nature, allows the insert to be folded lengthwise upon itself in halves, thirds, and even quarters so as to allow it to be shoved into a diaper bag or purse for storage. Whether the sleeve of the invention be constructed with one or two of these inserts, each of them is preferably constructed of a length and width equal to or slightly less than that of their respective linings. With the width of the sleeve being such as to provide a loose fit about the wearer's arm throughout its length, either or both of the two inserts (where they are employed), could be brought into play in supporting the infant's head, simply by rotating the sleeve about the wearer's arm. By appropriate selection of the thickness of the resilient cushion inserts, an ease in its folding comes about—especially when the thickness is of the order of ½ inch or less. With the composition of the sleeve fabric and cushion insert as set forth, the sleeve of the invention will be appreciated to be machine washable. In such embodiments, after washing, the sleeve of the invention could just be dried flat. Where it is desired for the sleeve to be machine dryable, in addition, the insert(s) could be secured between the linings as by a stitching, in preventing the insert(s) from sliding between the linings during the machine drying cycle. This further adds to the ability to fold the sleeve along its length, from one end towards the other, in allowing easy storage in the diaper bag or purse.

With either configuration or arrangement, the overall result is to provide the comfort for the mother and child, cushioning the baby's head, absorbing any perspiration that may be present, and providing a sleeve which is washable and durable, and which is comfortable both for the infant and the mother too, in the breast and bottle feeding of her baby.

While there have been described what are considered to be preferred embodiments of the present invention, it will be readily appreciated by those skilled in the art that modifications can be made without departing from the scope of the teachings herein. For at least such reason, therefore, resort should be had to the claims appended hereto for a true understanding of the scope of the invention.

I claim:

1. A washable, breast and bottle feeding infant head support foldable lengthwise upon itself in one of halves, thirds and quarters comprising:

a slip-on sleeve adapted for wearing on an arm, said sleeve being open at opposite ends thereof and having inner and outer linings running along the lengths of said sleeve, said inner linings and said outer linings forming first and second outwardly opposing face surfaces of predetermined length and width;

and a cushioning insert adapted for supporting the head of the infant, said insert being between said inner lining and an outer lining forming one of said outwardly opposing face surfaces, with said insert being of a length equal to or slightly less than the lengths of said linings forming said one outwardly opposing face surface; and wherein said sleeve, when worn on the arm, is of a length to extend past the crook of the wearer's elbow and towards the palm of the wearer's hand for the fingers to hold said sleeve in place, and is of a polyester composition for washing when removed from the arm;

wherein said sleeve and said cushion insert are of a soft fabrication to comfortably support the head of the infant resting upon said sleeve slipped on the wearer's arm during breast and bottle feeding;

wherein said opposite ends of said sleeve are of a dimension to afford both easy slide-in of said sleeve around the wearer's arm when feeding is to be had and easy slide-off of said sleeve from around the wearer's arm for storage when feeding has been completed;

wherein said sleeve, when worn, is of a width to loosely fit for rotation throughout its length about the wearer's arm;

wherein said cushion insert extends between said inner and outer linings forming said one outwardly opposing face surface along their respective lengths;

wherein said cushion insert is of a substantially rectangular configuration of polyurethane composition and thickness to support the head of the infant and, of a resilience to fold lengthwise upon itself in one of halves, thirds and quarters in storing the sleeve in a diaper bag or purse for carrying until a time of infant breast or bottle feeding is to occur; and whereby said sleeve is worn about the wearer's arm substantially only when said breast and bottle feeding of the infant occurs.

2. The washable infant head support of claim 1 wherein said slip-on sleeve is composed of a polyester MicroVelour fabric material.

3. The washable infant head support of claim 1 wherein said cushioning insert is of a foam padded material.

4. The washable infant head support of claim 3 wherein said cushion insert is composed of a hypoallergenic polyurethane material.

5. The washable infant head support of claim 3 wherein said cushion insert is composed of a hypoallergenic polyurethane material.

6. The washable infant head support of claim 5 wherein said cushion insert is secured between said inner and outer linings forming said one outwardly opposing face surface.

7. The washable infant head support of claim 1 including a second cushion insert between an inner lining and an outer lining forming the other outwardly opposing face surface, wherein said second cushion insert extends between the inner and outer linings forming said other outwardly opposing face surface along their respective lengths, with said second insert being of a length equal to or slightly less than the lengths of said linings forming said other outwardly opposing face surface, and wherein said second cushion insert is also of a substantially rectangular configuration of polyurethane composition and thickness to support the head of the infant and, of a resilience to fold lengthwise upon itself in one of halves, thirds and quarters in storing the sleeve in a diaper bag or purse for carrying until said time of infant breast or bottle feeding is to occur.

8. The infant head support of claim 7 wherein said slip-on sleeve is composed of a polyester MicroVelour fabric material and wherein each of said first and second cushion inserts is composed of a hypoallergenic polyurethane material.

* * * * *